United States Patent
Mimura et al.

(10) Patent No.: US 6,383,970 B1
(45) Date of Patent: May 7, 2002

(54) SOLID ACID CATALYST

(75) Inventors: Taku Mimura; Jun Kaita; Noriaki Fukuoka; Yasuyuki Hattori, all of Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 09/597,536

(22) Filed: Jun. 19, 2000

(30) Foreign Application Priority Data

Jun. 21, 1999 (JP) .......................................... 11-173953

(51) Int. Cl.$^7$ .......................... B01J 31/00; B01J 27/14; B01J 23/40; C07F 5/06; C07C 43/11
(52) U.S. Cl. ...................... 502/162; 502/208; 502/213; 502/327; 502/355; 554/162; 568/618
(58) Field of Search .................. 554/162; 568/618; 502/208, 202, 162, 172, 150, 213, 327, 355

(56) References Cited

U.S. PATENT DOCUMENTS

| | | | | | |
|---|---|---|---|---|---|
| 2,569,092 | A | * | 9/1951 | Deering | 502/213 |
| 3,697,496 | A | * | 10/1972 | Ueno et al. | 260/2 A |
| 4,202,798 | A | | 5/1980 | Johnson et al. | 252/437 |
| 4,251,350 | A | | 2/1981 | Johnson et al. | 208/216 R |
| 4,376,064 | A | * | 3/1983 | Hoff et al. | 252/429 B |
| 4,430,252 | A | | 2/1984 | Ryu | 502/162 |
| 4,464,539 | A | * | 8/1984 | Hashimoto et al. | 560/212 |
| 5,595,952 | A | * | 1/1997 | Maeda et al. | 502/162 |
| 5,880,058 | A | * | 3/1999 | Moriya et al. | 502/302 |
| 6,136,746 | A | * | 10/2000 | Tanielyan et al. | 502/154 |

OTHER PUBLICATIONS

Derwent Abstracts, Accession No. 86–233165/198636, JP–A 61–200943, Sep. 5, 1986.
Derwent Abstracts, Accession No. 94–343247/199443, EP0623581A2, Nov. 9, 1994.
Derwent Abstracts, Accession No. 87–207580/198730, JP–B 4–028250, May 13, 1992.
Derwent Abstracts, Accession No. 88–163115/198824, JP–A 63–146838, Jun. 18, 1988.
Derwent Abstracts, Accession No. 85–191160/198532, JP–A 60–188338, Sep. 25, 1985.

* cited by examiner

*Primary Examiner*—Mark L. Bell
*Assistant Examiner*—Patricia L. Hailey
(74) *Attorney, Agent, or Firm*—Oblon, Spivak, McClelland, Maier & Neustadt, P.C.

(57) ABSTRACT

The present invention provides a solid acid catalyst developing high activity and exhibiting high durability in various organic reactions. That is, the present invention provides a solid acid catalyst having the structure (A) in which a hydrogen atom is eliminated from at least one of OH groups contained in an inorganic phosphorus acid, the structure (B) in which a hydrogen atom is eliminated from at least one of OH groups contained in an organic phosphorus acid represented by the formula (1) or (2) and at least one metal atom (C) selected from aluminum, gallium and iron and a method for producing an ester, a ketal or an acetal by using the solid acid catalyst;

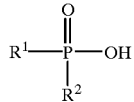

(1)

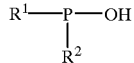

(2)

wherein each of —R$^1$ and —R$^2$ is selected from —R, —OR, —OH and —H in which at least one of —R$^1$ and —R$^2$ is —R or —OR, given that —R is an organic group having 1–22 carbon atoms.

17 Claims, 2 Drawing Sheets

SOLID ACID CATALYST

TECHNICAL FIELD

The present invention relates to a solid acid catalyst and to a method for producing an ester, a ketal or an acetal by using the solid acid catalyst.

PRIOR ART AND PROBLEMS TO BE SOLVED BY THE INVENTION

A solid acid catalyst has an advantage such as an easy operation for isolating a product after the reaction. Therefore, it is has been examined from the viewpoint of ability for use in various organic reactions. For example, there are known a zeolite (JP-A 61-200943), a silicate of the IV group elements (EP0623581A2), hydrous zirconium oxide (JP-B 4-28250) and the like for producing an ester and, then, an organic solid catalyst such as an ion-exchange resin and an inorganic solid catalyst such as hydrous zirconium oxide (JP-A 63-146838) and mordenite (JP-A 60-188338) for producing an acetal or a ketal. Those described in U.S. Pat. No. 4,202,798 and U.S. Pat. No. 4,251,350 are known.

In case a solid catalysts selected therefrom are used especially in a liquid phase reaction, the activity or the durability of the strength of formed catalyst can not satisfy, because of insufficient activity at a low temperature, elution of a catalytic component into the liquid phase, and the like.

It is an object of the present invention to provide a solid acid catalyst which develops its high activity and exhibits its high durability in various organic reactions.

DISCLOSURE OF THE INVENTION

The present invention relates to a solid acid catalyst having the following structure (A), structure (B) and metal atom (C) and to a method for producing an ester, a ketal or an acetal by using the solid acid catalyst.

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic phosphorus acid represented by the formula (1) or (2);

(1)

(2)

wherein each of —$R^1$ and —$R^2$ is selected from —R, —OR, —OH and —H in which at least one of —$R^1$ and —$R^2$ is —R or —OR, given that —R is an organic group having 1 to 22 carbon atoms;

Metal atom (C): at least one atom selected from aluminum, gallium and iron.

In this description, the structure (A) is derived from a phosphorus-containing compound (phosphorus acid) such as phosphonic acid, phosphorous acid, phosphinic acid, phosphoric acid, orthophosphoric acid and metaphosphoric acid, and other isomers or derivatives thereof. The phosphorus acid may be an oxy acid of phosphorus.

Further, the present invention provides the solid acid catalyst as mentioned above, wherein the structure (A) is a structure derived from orthophosphoric acid.

Furthermore, the present invention provides the solid acid catalyst as mentioned above, wherein the structure (B) is a structure derived from phosphonic acid.

Then, the present invention provides a method for producing an ester, which comprises producing an ester from a raw ester or raw carboxylic acid (a) and a raw alcohol (b) by using the catalyst as defined above.

The present invention provides also a method for producing a ketal or an acetal, which comprises producing a ketal or an acetal from a ketone or aldehyde (c) and an alcohol (d) by using the catalyst as defined above.

The present invention provides a method for preparing a solid acid catalyst having the following structure (A), structure (B) and metal atom(C);

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic phosphorus acid represented by the formula (1) or (2):

(1)

(2)

wherein each of —$R^1$ and —$R^2$ is selected from —R, —OR, —OH and —H in which at least one of —$R^1$ and —$R^2$ is —R or —OR, given that —R is an organic group having 1 to 22 carbon atoms;

Metal atom (C): at least one atom selected from aluminum, gallium and iron.

The present invention provides use of the catalyst as defined above for production of an ester compound.

The present invention provides use of the catalyst as defined above for production of a ketal compound or an acetal compound.

The catalyst of the invention may be that being obtainable from the inorganic phosphorus-containing compound for the structure (A), the organic phosphorus acid for the structure (B) and a metal compound for the metal (C).

MODES FOR CARRYING OUT THE INVENTION

In the structure (A) in the solid acid catalyst of the present invention, the inorganic phosphorus acid includes orthophosphoric acid, metaphosphoric acid and a condensed phosphoric acid such as pyrophosphoric acid. Orthophosphoric acid is preferable from the viewpoint of performance.

Also, in the structure (B), the organic phosphorus acid represented by the formula (1) or (2) includes phosphonic acid, phosphonic acid monoester, phosphinic acid, phosphoric acid monoester, phosphoric acid diester, phosphorous acid monoester and phosphorous acid diester. A mixture thereof may be included. Phosphonic acid is preferable.

The organic group —R in the organic phosphorus acid is preferable to be an alkyl group such as methyl, ethyl, n-propyl, iso-propyl, n-butyl, iso-butyl, tert-butyl, n-hexyl, 2-ethylhexyl, octyl, dodecyl and octadecyl or to be an aryl group such as phenyl and 3-methylphenyl. Also, one of these groups may be combined with an amino group, an alkoxy group, a carbonyl group, an alkoxycarbonyl group, a carboxyl group, a halogen group including chloro group, phosphono group, sulfo group or the like for use.

The metal atom (C) is preferably aluminum from the viewpoint of performance and/or cost. Then, it may contain a small amount of a metal atom other than aluminum, gallium and iron in order to improve selectivity or other performances.

From the viewpoint of performance, the ratio of the structure (A) to the structure (B) in the solid acid catalyst of the present invention is preferable in such ratio that the molecular ratio x of an organic phosphorus acid represented by the following formula (3) is 0.01 to 0.99. Here, [Pinorg] shows the molecular number of phosphorus atom contained in the structure (A) and [Porg] shows the molecular number of phosphorus atom contained in the structure (B).

$$x=[Porg]/([Pinorg]+[Porg]) \quad (3)$$

Then, a more preferable ratio is present in the ratio x depending upon a reaction to be utilized. The x is preferably 0.01 to 0.7 and more preferably 0.01 to 0.5 at the production of an ester. On the other hand, the x is preferably 0.05 to 0.99 and more preferably 0.1 to 0.8 at the production of a ketal or acetal.

Then, the value Y represented by the following formula (4) is preferably 0.15 to 2.0.

$$Y=[Metal]/([Pinorg]+[Porg]) \quad (4)$$

Here, [Metal] shows the number of the metal atoms (C) in the catalyst.

All of the metal atom (C) contained in the catalyst doesn't bond necessarily to the structure (A) or (B). Some of the metal atom (C) may be present in the form of a metal oxide, metal hydroxide or the like.

As the method for preparing the solid acid catalyst of the present invention, a precipitating method, a method for impregnating an inorganic phosphorus acid and an organic phosphorus acid onto a metal oxide or a metal hydroxide, and a method for substituting an inorganic phosphorus acid group in an inorganic phosphorus acid aluminum salt-gel for an organic phosphorus acid group or the like is used. The precipitating method is preferable. Then, the method for preparing the solid acid catalyst may comprise merely mixing a powder of an inorganic phosphorus acid salt with another powder of an organic phosphorus acid salt, as it is, homogeneously. Here, the powder of the inorganic phosphorus acid salt may comprise the above-mentioned structure (A) and the metal atom (C), and the other powder of the organic phosphorus acid salt may comprise the above-mentioned structure (B) and the metal atom (C). In the precipitating method, a precipitate of the present catalyst is obtained by mixing an aqueous solution (S) of a water-soluble salt of aluminum, an inorganic phosphorus acid and an organic phosphorus acid with an alkali (T) such as an aqueous solution of ammonia, an aqueous solution of sodium carbonate and an aqueous solution of sodium hydroxide and then regulating the pH. Also, there is no limit of order for adding the aqueous solution (S) and the alkali (T). Further, in case the organic phosphorus acid has poor water-solubility, the aqueous solution (S) may be prepared by properly adding a solvent such as methanol and acetone. The obtained precipitate is dried and, if necessary, further calcinated. At this time, calcination at a high temperature causes possibility of losing an organic group in the structure derived from the organic phosphorus acid. Hence calcination at a temperature of 600° C. or lower is preferable and at a temperature of 500° C. or lower is more preferable.

Also, it is possible to obtain a catalyst supported on a carrier by making the carrier having its large surface-area coexist at when the catalyst of the present invention is prepared. As the carrier, silica, alumina, silica-alumina, titania, zirconia, an activated carbon or the like may be used. The use of excessive carrier decreases the content of an active component to decrease the activity. Therefore, the proportion of the carrier in the catalyst is preferably 90% by weight or less.

It is possible that the form of the catalyst is powder for use, as it is, to disperse in a raw material. On the other hand, it is possible that the form of the catalyst is formed into a proper granule or shape and charged in a reaction-column to carry out the continuous reaction.

It is necessary and essential that the solid acid catalyst of the present invention has the structures (A) and (B) simultaneously in the condition under which the catalyst is used for a reaction. However, it is unnecessary to have all of the inorganic phosphorus acid and organic phosphorus acid which have been used for the preparation.

The solid acid catalyst of the present invention can be utilized in various catalytic reactions. For example, the catalytic reaction includes a transesterification, an esterification, a formation of an acetal from an aldehyde and an alcohol or a formation of a ketal from a ketone and an alcohol, an aldol condensation, an amidation, an amination, a synthesis of an olefin or ether by dehydrating an alcohol or alcohols, a hydration of an olefin and an addition to olefin with an alcohol, an isomerization and an alkylation or acylation of an aromatic ring, and the like.

As to each of reaction-conditions in the various reactions mentioned above, for example, the optimum condition of the reaction phase (vapor phase or liquid phase) is selected according to the type of reaction. Since the solid acid catalyst of the present invention exhibits its high activity even in a mild condition, it is preferably used not only in a vapor phase but also in a liquid phase-condition where a conventional solid catalyst develops its high activity with difficulty. Also, for example, the optimum condition of the reaction-pressure is selected in accordance with the type of reaction. The reaction may be carried out under pressurization, atmospheric pressure or reduced pressure. Also, the reaction-temperature is preferable not to lose the organic groups in the structure (B), for instance. For example, in the presence of oxygen, the catalyst is used preferably at 600° C. or less and more preferably at 500° C. or less.

In a transesterification or an esterification, the solid acid catalyst of the present invention exhibits very high activity and good selectivity and, further, can maintain its activity and selectivity for a long period. As the result, a highly pure ester can be obtained in a short reaction-time with high yield over a long term.

A transesterification or esterification is carried out by mixing a raw ester or raw carboxylic acid (a) with a raw alcohol (b) and bringing the resultant mixture into contact with the solid acid catalyst of the present invention under a reaction-condition.

As the raw ester among the raw ester or raw carboxylic acid (a), an ester or partial ester, for example, of a $C_{1-22}$ linear or branched aliphatic carboxylic acid or aromatic carboxylic acid or a mixture thereof with a $C_{1-22}$ linear or branched monohydric or polyhydric alcohol is used. Specifically, such an ester or partial ester is produced from a carboxylic acid or dicarboxylic acid such as acetic acid, butyric acid, caproic acid, caprylic acid, capric acid, lauric acid, myristic acid, palmitic acid, oleic acid, stearic acid and benzoic acid or a mixture thereof with a monohydric aliphatic alcohol such as methanol, ethanol, propanol, butanol, octanol and stearyl alcohol; a monohydric aromatic alcohol such as phenol or a polyhydric alcohol such as ethylene glycol, propylene glycol, glycerol, pentaerythritol and sorbitol. It is preferable to be a natural vegetable (plant and so on) oil such as a monoglyceride, a diglyceride, a triglyceride, coconut oil, palm oil and palm-kernel oil or an animal oil such as beef-tallow and pork-lard. Also, as the raw carboxylic acid, the above-mentioned $C_{1-22}$ linear or branched aliphatic carboxylic acid or aromatic carboxylic acid or a mixture thereof is used.

Also, as the raw alcohol (b), the above-mentioned $C_{1-22}$ linear or branched monohydric or polyhydric alcohol is used.

The esterifying method includes, for example, those in which the raw ester or raw carboxylic acid (a) and the raw alcohol (b) are continuously fed into a reaction-column charged with a solid acid catalyst and those in which the raw ester or raw carboxylic acid (a) and the raw alcohol (b) are bought into contact with a solid acid catalyst in a reaction-chamber to react in batch-wise. At this time, even only filtration satisfies a treatment after the reaction. Therefore, a neutralizing step and catalyst-removing step which are required in the case of using a homogeneous catalyst used in general can be omitted. Also, the recovery of un-reacted raw materials is made easy.

With regard to the reaction-pressure and temperature, a preferable condition can be selected according to the objective reaction. As to the reaction-temperature, it is preferable to carry out a reaction at a lower temperature in case of taking consideration of a side reaction. The solid acid catalyst of the present invention exhibits higher activity, as compared with a conventional solid acid catalyst, in an esterification even at a lower temperature-condition. Therefore, it is possible to obtain an objective ester at high selectivity.

The solid acid catalyst of the present invention also exhibits very high activity and good selectivity in an acetal- or ketal-formation of the ketone or aldehyde (c) and the alcohol (d) and further can maintain its activity and selectivity for a long period. As the result, a highly pure acetal or ketal can be obtained in a short reaction-time with high yield over a long term.

As the ketone or aldehyde (c), a $C_{1-22}$ linear or branched aliphatic ketone or aldehyde, or an aromatic ketone or aldehyde or the like is used. More specifically, acetone, methyl ethyl ketone, 3-pentanone, 2-pentanone, di-n-hexyl ketone, cyclohexanone, acetophenone, acetaldehyde, propionaldehyde, n-hexanal, n-dodecanal, benzaldehyde and the like may be exemplified.

Also, as the alcohol (d), the same alcohol as the raw alcohol (b) exemplified for the above-mentioned esterification is used.

A ketal- or acetal-forming method includes, for example, those in which the ketone or aldehyde (c) and the alcohol (d) are continuously fed into a reaction-column charged with a catalyst, those in which the reaction is carried out in a reaction-chamber in batch-wise and so on. At this time, a proper azeotropic solvent such as benzene and heptane is used to distill away the generated water, that may make the reaction-rate or the equilibration of the reaction advantageous.

If the solid acid catalyst of the present invention is used, even only filtration satisfies a treatment after the reaction. Therefore, a neutralizing step which is required in the case of using a homogeneous catalyst, such as paratoluenesulfonic acid and a mineral acid, used in general can be omitted. Also, in the distillation, no side reaction and the like due to the presence of a salt takes place. Therefore, the yield in a refining time can be improved and further the recovery of an un-reacted raw material is made easy.

The solid acid catalyst of the present invention has an organic group on the surface of the solid. Therefore, the active site on the surface of the catalyst has high affinity to an organic reactant and hence the catalyst is highly active.

This catalyst may be utilized in various catalytic reactions. Particularly, for producing an ester by esterification or transesterification and for producing a ketal or acetal by an acetal- or ketal-forming reaction, the catalyst can be easily separated from the products and makes it possible to obtain the product with high yield at high selectivity over a long term.

EXAMPLES

Example 1-1

(Preparation of a Catalyst)

14.2 g of phenylphosphonic acid, 27.7 g of 85% orthophosphoric acid and 112.5 g of aluminum nitrate (hydrated with nine moles per mole thereof) were dissolved in 1000 g of water and 80 g of methanol. An aqueous solution of ammonia was added dropwise into the resultant mixed solution at room temperature to raise the pH to 5. A gel-like white precipitate was generated on the way. The precipitate was filtered, washed with water and then dried at 110° C. for 15 hours. The dry precipitate was crushed into powder having the size of 60 meshes or less and the resultant powder was calcinated at 250° C. for 3 hours to obtain a solid acid catalyst.

Figure 1:
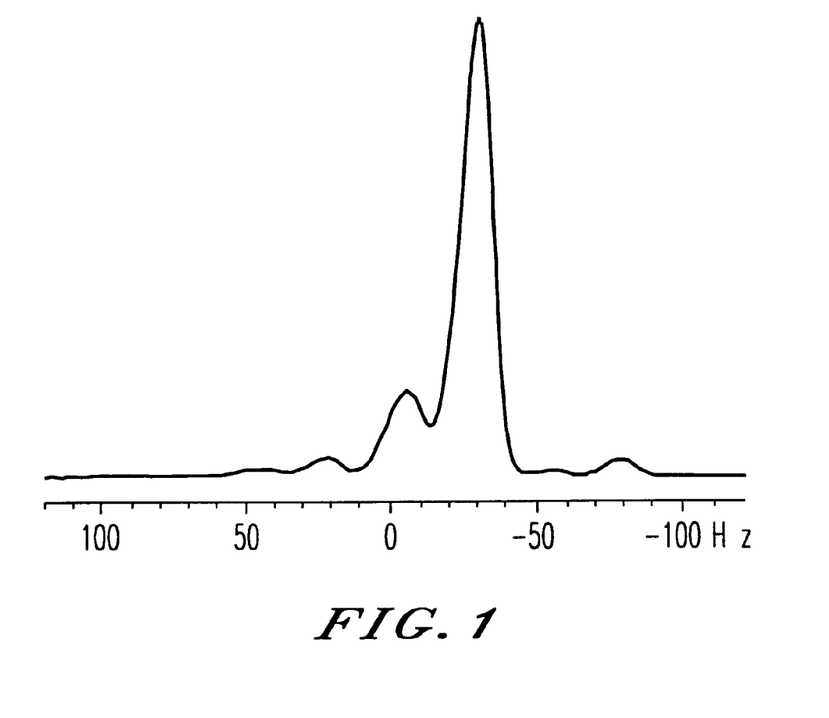
FIG. 1 is the P-NMR spectrum of the catalyst obtained in Example 1-1.

The obtained catalyst was analyzed from the viewpoint of the composition. The result is shown in Table 1. The analysis of the composition was carried out by using an analyzer (ICPS1000III, manufactured by Shimadzu Corporation) with ICP for a metal and P (phosphorus) and by using a CHN elemental analyzer (2400-2, manufactured by Perkin-Elmer) for C (carbon). Then, the P-NMR (using UNITY INOVA 300, manufactured by Varian) of the obtained catalyst was analyzed to obtain the result shown in FIG. 1. It was recognized that two peaks coexist. A peak (−29.2 Hz) was originated from P in the structure derived from orthophosphoric acid and another peak (−5.2 Hz) was originated from P in the structure derived from phenylphosphonic acid. Each of these peaks was identified by comparison with the peaks of aluminum phenyl phosphonate prepared in Comparative Example 1-1 described below and aluminum phosphate prepared in Comparative Example 1-2 described below and further by comparison with the data of literature (Inorg. Chem., 37 (1998), 4168, etc.).

Also, [Pinorg] and [Porg] being present in the catalyst were calculated based on the results obtained by the analysis of the compositions with viewpoint of C and P to determine the molar ratio x of organic phosphorus acid shown by the above-mentioned formula (3). The result is shown in Table 1.

Example 1-2
(Preparation of a Catalyst)

A solid acid catalyst was obtained in the same method as in Example 1-1 except that the type and amount of the raw materials to be fed and the condition for the preparation were changed to those shown in Table 1. In Table 1 was shown the data analyzed from the viewpoint of the composition and the molar ratio x of the organic phosphorus acid of the obtained catalyst.

Figure 2:
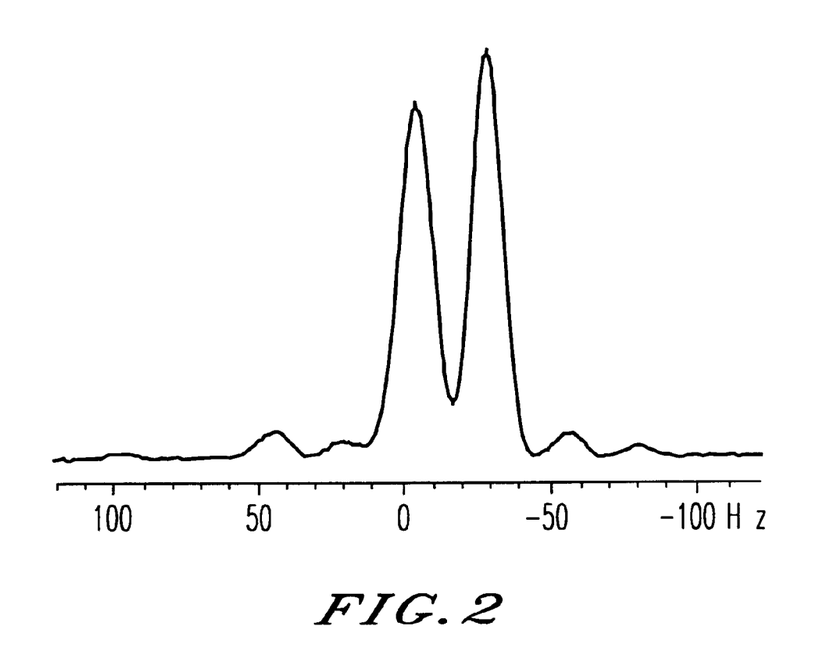
FIG. 2 is the P-NMR spectrum of the catalyst obtained in Example 1-2.

Also, the P-NMR of the obtained catalyst was analyzed to obtain the result shown in FIG. 2. It was recognized that two peaks coexist. A peak (−29.8 Hz) was originated from P in the structure derived from orthophosphoric acid and another peak (−5.3 Hz) was originated from P in the structure derived from phenylphosphonic acid.

Examples 1-3 to 1-8
(Preparation of Catalysts)

A solid acid catalyst was obtained in the same method as in Example 1-1 except that the type and amount of the raw materials to be fed and the condition for the preparation were changed to those shown in Table 1. In Table 1 was shown the data analyzed from the viewpoint of the composition and the molar ratio x of the organic phosphorus acid of the obtained catalyst.

Comparative Example 1-1
(Preparation of a Catalyst)

47.4 g of phenylphosphonic acid and 75.0 g of aluminum nitrate (hydrated with none moles of water per mole thereof) were dissolved in 800 g of water and 160 g of methanol. An aqueous solution of ammonia was added dropwise into the resultant mixed solution at room temperature to raise the pH to 4. A gel-like white precipitate was generated on the way. The precipitate was filtered, washed with water and dried at 110° C. for 15 hours. The dry precipitate was crushed into powder having the size of 60 meshes or less and the resultant powder was calcinated at 250° C. for 3 hours to obtain a catalyst.

Figure 3:
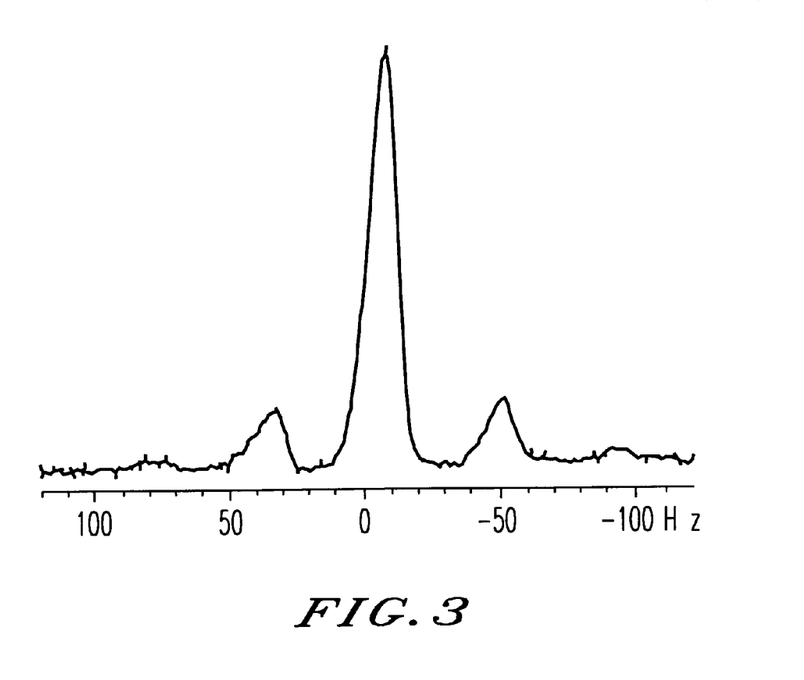
FIG. 3 is the P-NMR spectrum of the catalyst obtained in Comparative Example 1-1.

The obtained catalyst was analyzed from the viewpoint of the composition. The result is shown in Table 1. Then, the P-NMR of the obtained catalyst was analyzed to obtain the result shown in FIG. 3. It was recognized that a peak originated from the structure derived from phenylphosphonic acid existed at −9.5 Hz.

Comparative Example 1-2
(Preparation of a Catalyst)

563 g of 85% orthophosphoric acid and 173 g of aluminum nitrate (hydrated with nine moles of water per mole thereof) were dissolved in 5000 g of water. An aqueous solution of ammonia was added dropwise into the resultant mixed solution at room temperature to raise the pH to 7. A gel-like white precipitate was generated on the way. The precipitate was filtered, washed with water and dried at 110° C. sufficiently. The dry precipitate was crushed into powder having the size of 60 meshes or less and the resultant powder was calcinated at 400° C. for 3 hours to obtain a catalyst.

Figure 4:
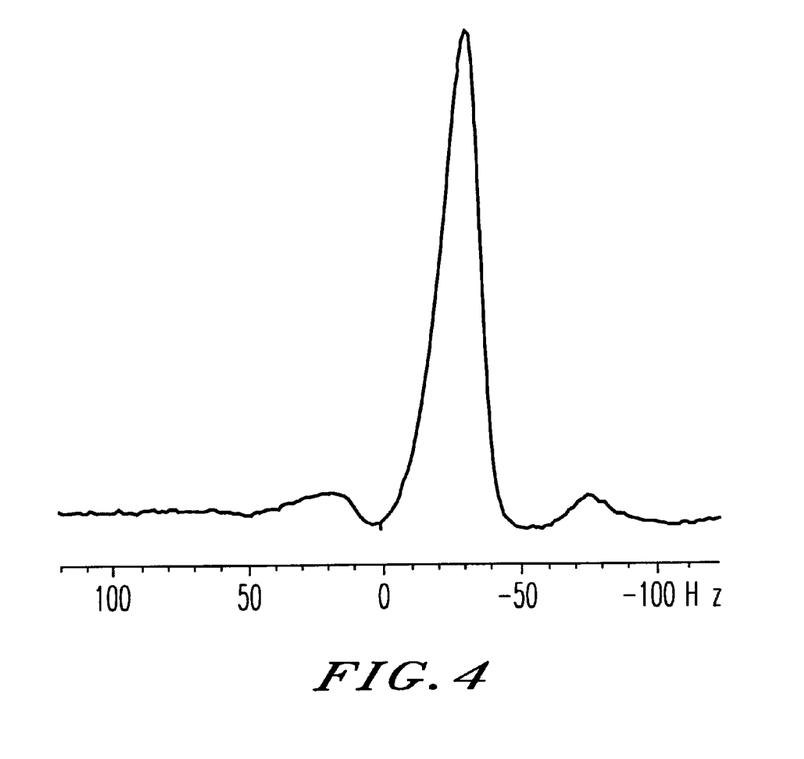
FIG. 4 is the P-NMR spectrum of the catalyst obtained in Comparative Example 1-2.

The obtained catalyst was analyzed from the viewpoint of the composition. The result is shown in Table 1. Then, the P-NMR of the obtained catalyst was analyzed to obtain the result shown in FIG. 4. It was recognized that a peak originated from the structure derived from orthophosphoric acid existed at −28.4 Hz.

TABLE 1

|  | Examples | | | | | | | | Comparative Examples | |
| --- | --- | --- | --- | --- | --- | --- | --- | --- | --- | --- |
|  | 1-1 | 1-2 | 1-3 | 1-4 | 1-5 | 1-6 | 1-7 | 1-8 | 1-1 | 1-2 |
| The amount to be fed (g) | | | | | | | | | | |
| Phenylphosphonic acid | 14.2 | 18.9 | 49.8 | 7.1 | — | — | 8.7 | 14.2 | 47.4 | — |
| Ethyl phosphonic acid | — | — | — | — | 9.9 | — | — | — | — | — |
| Tert-butylphosphonic acid | — | — | — | — | — | 9.7 | — | — | — | — |
| 85% Orthophosphoric acid | 27.7 | 10.9 | 10.4 | 31.1 | 27.7 | 8.1 | 16.9 | 27.7 | — | 563 |
| Aluminum nitrate (hydrated with nine moles of water per mole thereof) | 112.5 | 67.1 | 112.5 | 112.5 | 112.5 | 43.9 | — | — | 75 | 173 |
| Gallium nitrate (hydrated with eight moles of water per mole thereof) | — | — | — | — | — | — | 50.0 | — | — | — |
| Iron (III) nitrate (hydrated with nine moles of water per mole thereof) | — | — | — | — | — | — | — | 121.2 | — | — |
| Water | 1000 | 800 | 1000 | 1000 | 1000 | 400 | 600 | 1000 | 800 | 5000 |
| Methanol | 80 | 60 | 80 | 80 | — | — | 49 | 80 | 160 | — |
| Condition for preparation | | | | | | | | | | |
| pH | 5 | 4 | 5 | 5 | 5 | 5 | 5 | 4 | 4 | 7 |
| Temperature for calcination | 250° C. | 250° C. | 250° C. | 250° C. | 250° C. | 250° C. | 250° C. | 250° C. | 250° C. | 400° C. |
| Time for calcination | 3 Hr | 3 Hr | 3 Hr | 3 Hr | 3 Hr | 3 Hr | 3 Hr | 3 Hr | 3 Hr | 3 Hr |
| Composition of catalysts (% by weight) | | | | | | | | | | |
| metal | 18 | 14 | 13 | 21 | 16 | 18 | 36 | 25 | 10 | 20 |
| P | 22 | 17 | 18 | 23 | 19 | 20 | 17 | 15 | 15 | 20 |
| C | 8.5 | 20.9 | 30.6 | 4.2 | 2.5 | 10.1 | 1.7 | 9.9 | 38.5 | 0 |
| Molar ratio of organic phosphorus acid (x) | 0.17 | 0.53 | 0.73 | 0.079 | 0.17 | 0.33 | 0.043 | 0.284 | — | — |

Examples 2-1 to 2-6 and Comparative Examples 2-1 to 2-4

(Esterification)

An autoclave was fed with 200 g of palm-kernel oil (triglyceride), 55.8 g of methanol and 10 g of each of the solid acid catalysts prepared in Example 1-1 and Examples 1-4 to 1-8 as the catalyst of the present invention and catalysts prepared in Comparative Examples 1-1 and 1-2, hydrous zirconium oxide obtained by calcinating zirconium hydroxide (manufactured by Daiichi Kigenso Kagaku Kogyo Co., Ltd) at 300° C. for 2 hours in air and mordenite (manufactured by Tosoh Corp.) as the comparative catalyst. The suspension-reaction was carried out at the reaction-temperature of 200° C. for 5 hours under the condition closed tightly and then the catalyst was filtered out. The composition of the resultant solution after the reaction was analyzed using a gas chromatography to determine the yield of an ester when 5 hours passed from the start of the reaction. The reaction-rate represented by the following formula (4) was also determined. The result is shown in Table 2. Incidentally, the yield of an ester is 81.7%, when the reaction is equilibrated.

$$\text{Reaction-rate } [1/hr] = [\ln((EV_0 - EV_e)/(EV_{5h} - EV_e))]/5 \qquad (4)$$

Here, $EV_0$ represents the ester value (KOH mg/g) of a raw triglyceride, $EV_e$ represents an equilibrated ester value (KOH mg/g) and $EV_{5h}$ represents the ester value (KOH mg/g) of a glyceride being left in the reaction-solution when 5 hours passed from the start of the reaction.

Comparative Example 3-2

(Esterification)

A catalyst molded by extruding titanosilicate [Ti/Si=1/9.2, prepared by an alkoxide method (see "Preparation of Catalysts Using Metal Alkoxides", P303, Akihumi Ueno et al., IPC)] with a noodle-like form was filled in a reaction-column to continuously react a palm-kernel oil (triglyceride) with methanol on a fixed bed. The reaction was carried out under the following condition which was more advantageous than that in Example 3-1 in view of proceeding the reaction: the temperature of 200° C., the molar ratio of methanol/triglyceride being 60 [mol/mol], LHSV of 0.2 [1/hr]. The yield of an ester and the reaction-rate represented by the above-mentioned formula (5) are shown in Table 3.

TABLE 3

|  | Examples | | Comparative examples | |
|---|---|---|---|---|
|  | 3-1 | 3-2 | 3-1 | 3-2 |
| Esterification Catalyst | Example 1-1 | Example 1-5 | Comparative example 1-2 | Titano-silicate |
| The yield of an ester (%) | 78.0 | 84.7 | 60.4 | 54.3 |
| Reaction-rate | 0.69 | 0.81 | 0.39 | 0.18 |

TABLE 2

|  | Examples | | | | | | Comparative examples | | | |
|---|---|---|---|---|---|---|---|---|---|---|
|  | 2-1 | 2-2 | 2-3 | 2-4 | 2-5 | 2-6 | 2-1 | 2-2 | | |
| Esterification Catalyst | Example 1-1 | Example 1-4 | Example 1-5 | Example 1-6 | Example 1-7 | Example 1-8 | Comparative Example 1-1 | Comparative Example 1-2 | Hydrous zirconium oxide | 2-4 Mordenite |
| The yield when 5 hours passed from the start of the reaction (%) | 78.8 | 76.5 | 79.0 | 81.2 | 71.6 | 70.4 | 59.3 | 69.3 | 45 | 18 |
| Reaction-rate | 0.71 | 0.59 | 0.81 | 1.31 | 0.44 | 0.42 | 0.25 | 0.39 | 0.18 | 0.08 |

Examples 3-1 and 3-2 and Comparative Example 3-1

(Esterification)

Using the solid acid catalysts prepared in Examples 1-1 and 1-5 as the catalyst of the present invention and the catalyst prepared in Comparative Example 1-2 as the comparative catalyst, each of these catalysts was molded by extrusion into a noodle-like form and the molded catalyst was filled in a reaction-column to continuously react a palm-kernel oil (triglyceride) with methanol on a fixed bed. The reaction was carried out under the following condition: the temperature of 170° C., the molar ratio of methanol/triglyceride being 10 [mol/mol], LHSV of 0.2 [1/hr]. The yield of an ester and the reaction-rate represented by the following formula (5) are shown in Table 3. Incidentally, the yield of an ester is 95.5%, when the reaction is equilibrated.

$$\text{Reaction-rate} = \ln((EV_{inlet} - EV_e)/(EV_{outlet} - EV_e)) \qquad (5)$$

Here, $EV_{inlet}$ represents the ester value (KOH mg/g) of a raw triglyceride, $EV_e$ represents an equilibrated ester value (KOH mg/g) and $EV_{outlet}$ represents the ester value (KOH mg/g) of a glyceride being left in the reaction-solution at the outlet of the reaction-column.

Examples 4-1 and 4-2

(Esterification)

Using the solid acid catalyst prepared in Example 1-5, the continuous operation was carried out for a long period under the same condition as in Example 3-2 with the multiple for the passed solution (the ratio of the weight of the raw triglyceride having passed through for the period still then as compared with the weight of the catalyst filled in the reaction-column) shown in Table 4. The result is shown in Table 4. It is clear from Table 4 that the conversion rate (yield of an ester) of triglyceride was kept high.

TABLE 4

| Esterification Catalyst | | The multiple for the passed solution (the mutiple) | Yield of an ester at the outlet of the reaction-column (%) | Reaction-rate |
|---|---|---|---|---|
| Example 4-1 | Example 1-5 | 230 | 84.7 | 2.4 |
| Example 4-2 | Example 1-5 | 1250 | 84.9 | 2.4 |

Example 5-1

(Ketal-forming Reaction)

A flask having its capacity of 200 ml was charged with 32.4 g of methyl ethyl ketone, 27.6 g of glycerol, 13.2 g of heptane and 3.75 g of the solid acid catalyst prepared in Example 1-1 as catalyst. The temperature of the resultant mixture was raised using an oil bath. Heptane and water started to be distilled at about 100° C. Then, the temperature was raised gradually while the amount of reflux was kept constant. The progress of the reaction was traced by the amount of the distilled water. In this case, methyl ethyl ketone was dissolved in an amount of about 20% in the distilled water. The reaction-rate was compared based on the distillation-rate of the distilled water. The result is shown in Table 5. The time required for the amount of the distilled water to reach 6 ml implies that the shorter the time is, the higher the activity of the reaction is.

The reaction was completed in 5 hours and the amount of the distilled water at that time was 6.2 ml.

Thereafter, the catalyst was removed by filtration and a ketal of glycerol was obtained by distillation. The yield of the ketal was 93.7% and the selectivity thereof was 98.4%.

Examples 5-2 and 5-3

(Ketal-forming Reaction)

The reaction was carried out in the same method as in Example 5-1 except that the solid acid catalysts prepared in Examples 1-2 and 1-3 were used as catalyst. The result of the comparison of the distillation-rate of the distilled water is shown in Table 5.

Comparative Example 5-1

(Ketal-forming Reaction)

The reaction was carried out in the same method as in Example 5-1 except that the catalyst prepared in Comparative Example 1-1 was used as catalyst. The result of the comparison of the distillation-rate of the distilled water is shown in Table 5. Thereafter, the catalyst was removed by filtration and a ketal of glycerol was obtained by distillation. The yield of the ketal was 89.2% and the selectivity thereof was 97.6%.

Comparative Example 5-2

(Ketal-forming Reaction)

The reaction was carried out in the same method as in Example 5-1 except that the catalyst prepared in Comparative Example 1-2 was used as catalyst. The result of the comparison of the distillation-rate of the distilled water is shown in Table 5. The catalyst was removed by filtration after 5.0 hours passed from the start of the reaction and a ketal of glycerol was obtained by distillation. The yield of the ketal was 40.5%.

Comparative Example 5-3

(Ketal-forming Reaction)

The reaction was carried out in the same method as in Example 5-1 except that the same hydrous zirconium oxide as one used in Comparative Example 2-3 was used as catalyst. The result of the comparison of the distillation-rate of the distilled water is shown in Table 5.

TABLE 5

| Ketal-forming reaction Catalyst | Examples | | | Comparative Examples | | |
|---|---|---|---|---|---|---|
| | 5-1 Example 1-1 | 5-2 Example 1-1 | 5-3 Example 1-3 | 5-1 Comparative Example 1-1 | 5-2 Comparative Example 1-2 | 5-3 Hydrous Zirconium oxide |
| Time required for the amount of the distilled water to reach 6 ml (hr) | 3.30 | 3.25 | 3.28 | 5.0 | Amount of distilled water for 5.0 hours: 2.9 ml | Amount of distilled water for 5.0 hours: about 0 ml |

Example 6-1

(Esterification)

The solid acid catalyst obtained in Example 1-5 was extruded into the shape of noodles. A reaction column was filled with the catalyst. A continuous reaction was effected between a fatty acid and methanol on the fixed bed thereof at 200° C., at the internal pressure of 1.0 Mpa, at the mole ratio of methanol to the fatty acid of 3[mol/mol], at an LHSV of 0.5 [1/hr]. The used fatty acid was a mixture of lauric acid and myristic acid, having an acid value of 270 KOH-mg/g.

Methanol and water were distilled out of the liquid obtained from the reaction column and fatty acid methyl esters were obtained at a production yield of 90.5%. The crude product of the methyl esters was then treated for further reaction at 200° C. at the internal pressure of 1.0 Mpa at the mole ratio of methanol to the fatty acid and the methyl esters in total being 3 [mol/mol] at an LHSV of 1 [1/hr]. Methanol and water were distilled out of the liquid obtained from the reaction column and the fatty acid methyl esters were obtained at a production yield of 99.7%.

What is claimed is:

1. A solid acid catalyst having the following structure (A), structure (B) and metal atom (C);

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic phosphorus acid represented by the formula (1) or (2):

wherein each of —R¹ and —R² is selected from —R, —OR, —OH and —H in which at least one of —R¹ and —R² is —R or —OR, given that —R is an organic group having 1 to 22 carbon atoms;

Metal atom (C): at least one atom selected from aluminum, gallium and iron.

2. The solid acid catalyst as claimed in claim 1, wherein the structure (A) is a structure derived from orthophosphoric acid.

3. The solid acid catalyst as claimed in claim 1 or 2, wherein the structure (B) is a structure derived from phosphonic acid.

4. A method for producing an ester comprising contacting a raw ester or raw carboxylic acid (a) and a raw alcohol (b) with the catalyst as defined in claim 1 or 2.

5. The method of claim 4, wherein the structure (B) is a structure derived from phosphonic acid.

6. The method of claim 4, wherein the structure (A) is a structure derived from orthophosphoric acid and the structure (B) is a structure derived from phosphonic acid.

7. A method for producing a ketal or an acetal, which comprises contacting a ketone or aldehyde (c) and an alcohol (d) with the catalyst as defined in claim 1 or 2.

8. The method of claims 7, wherein the structure (B) is a structure derived from phosphonic acid.

9. The method of claim 7, wherein the structure (A) is a structure derived from orthophosphoric acid and the structure (B) is a structure derived from phosphonic acid.

10. The solid acid catalyst of claim 1, having a molar ratio x, wherein $x = P_{org}/(P_{inorg} + P_{org}) = 0.01$ to $0.99$, wherein $P_{inorg}$ shows the molecular number of phosphorus atoms contained in said structure (A) and $P_{org}$ shows the molecular number of phosphorus atoms contained in said structure (B).

11. The solid acid catalyst of claim 10, wherein $x = 0.01$ to $0.7$.

12. The solid acid catalyst of claim 10, wherein $x = 0.01$ to $0.5$.

13. The solid acid catalyst of claim 10, wherein $x = 0.05$ to $0.99$.

14. The solid acid catalyst of claim 10, wherein $x = 0.1$ to $0.8$.

15. A method for preparing a solid acid catalyst having the following structure (A), structure (B) and metal atom (C);

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic groups contained in an organic phosphorus acid represented by the formula (1) or (2):

wherein each of —R¹ and R² is selected from —R, —OR, —OH and —H in which at least one of —R¹ and —R² is —R or —OR, given that —R is an organic group having 1 to 22 carbon atoms;

Metal atom (C): at least one atom selected from aluminum, gallium and iron, comprising precipitating said solid acid catalyst from an aqueous solution of water-soluble metal salt, inorganic phosphorous acid and organic phosphorus acid, with alkali.

16. A method for preparing a solid acid catalyst having the following structure (A), structure (B) and metal atom (C);

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic groups contained in an organic phosphorus acid represented by the formula (1) or (2):

wherein each of —R¹ and R² is selected from —R, —OR, —OH and —H in which at least one of —R¹ and —R² is —R or —OR, given that —R is an organic group having 1 to 22 carbon atoms;

Metal atom (C): at least one atom selected from aluminum, gallium and iron, comprising impregnating an inorganic phosphorous acid and an organic phosphorus acid onto a metal oxide or a metal hydroxide.

17. A method for preparing a solid acid catalyst having the following structure (A), structure (B) and metal atom (C);

Structure (A): a structure in which a hydrogen atom is eliminated from at least one of OH groups contained in an inorganic phosphorus acid;

Structure (B): a structure in which a hydrogen atom is eliminated from at least one of OH groups contained in an organic groups contained in an organic phosphorus acid represented by the formula (1) or (2):

(1)

(2)

wherein each of —$R^1$ and $R^2$ is selected from —R, —OR, —OH and —H in which at least one of —$R^1$ and —$R^2$ is —R or —OR, given that —R is an organic group having 1 to 22 carbon atoms;

Metal atom (C): at least one atom selected from aluminum, gallium and iron, comprising substituting an inorganic phosphorous acid group in an inorganic phosphorus acid metal salt-gel for an organic phosphorus acid group.

* * * * *